United States Patent [19]

Shirafuji et al.

[11] Patent Number: 4,879,422

[45] Date of Patent: Nov. 7, 1989

[54] METHOD FOR PRODUCING CYCLOALKANOL

[75] Inventors: Tamio Shirafuji; Kiyomi Sakai, both of Niihama, Japan

[73] Assignee: Sumitomo Chemical Company, Limited, Osaka, Japan

[21] Appl. No.: 211,881

[22] Filed: Jun. 27, 1988

[30] Foreign Application Priority Data

Jul. 7, 1987 [JP] Japan .................................. 62-170027

[51] Int. Cl.$^4$ ............................................. C07C 29/04
[52] U.S. Cl. ..................................... 568/835; 568/895
[58] Field of Search .......................................... 568/895

[56] References Cited

U.S. PATENT DOCUMENTS 4,507,512  4/1985  Okumura et al. .................... 568/895
4,528,409  7/1985  Mitsui et al. ......................... 568/835
4,588,846  5/1986  Mitsui et al. ......................... 568/895
4,595,786  7/1986  Waller ................................. 568/895
4,716,243 12/1987  Shirafuji et al. ..................... 568/895

FOREIGN PATENT DOCUMENTS 0162475  11/1985  European Pat. Off. ............ 568/835
59-222431 12/1984  Japan .................................. 568/895
60-104030  6/1985  Japan .................................. 568/895
60-248633 12/1985  Japan .................................. 568/895

Primary Examiner—Werren B. Lone
Attorney, Agent, or Firm—Stevens, Davis, Miller & Mosher

[57] ABSTRACT

A method for producing a cycloalkanol in high yield by hydrating cycloalkene with a specific catalyst is disclosed. The catalyst is obtainable by ion-exchanging all or a part of the cations of a crystalline gallium silicate with hydrogen ions. It has a specific composition defined by the general formula and is characterized by the X-ray diffraction pattern.

11 Claims, No Drawings

METHOD FOR PRODUCING CYCLOALKANOL

The present invention relates to a method for producing a cycloalkanol which comprises hydrating a cycloalkene with an inorganic solid acid catalyst.

Methods for producing a cycloalkanol by hydrating a cycloalkene with an inorganic solid acid catalyst have already been known.

JP-B-47-45323 proposes a method using dealkalized mordenite, clinoptilolite or faujasite zeolite as a catalyst.

JP-A-58-194828 proposes a method using a crystalline aluminosilicate having a molar ratio of silica to alumina of 20 or more.

JP-A-59-222431 proposes a method using a hydrogen-type mordenite or hydrogen-type zeolite Y having a molar ratio of silica to alumina of 20-500.

JP-A-60-104029 proposes a method using mordenite, faujasite or ferrierite zeolite having a molar ratio of silica to alumina of 20 or more.

JP-A-60-104030 proposes a method using a catalyst which is obtainable by substituting hydrogen ions for a part or all of the alkaline metal ions and/or ammonium ions of a crystalline aluminosilicate having a composition corresponding to the general formula, $M_2O\cdot Al_2O_3\cdot xSiO_2$ (wherein M represents at least one member selected from alkaline metal ions, ammonium ion and hydrogen ion, x is 10–1,000), and characterized in that X-ray diffractometry thereof shows specific relative intensities at specific angles of diffraction ($2\theta$).

JP-A-61-180735 proposes a method using a crystalline aluminosilicate synthesized in the coexistence of a lower alkylated urea or a lower alkylated thiourea.

JP-A-61-221141 proposes a method using a crystalline aluminosilicate synthesized in the coexistence of a lower cyanoalkane or a lower cyanoalkene.

However these conventional methods are not satisfactory in industry because they give only a low yield of cycloalkanol.

In view of such circumstances, the present inventors have made extensive study on a method for producing a cycloalkanol in high yield with an inorganic solid acid catalyst. As the result, they have found that the method using as a catalyst a crystalline gallium silicate of which the ion-exchangeable cations are wholly or partly ion-exchanged by hydrogen ions gives a high yield of cycloalkanol. The present invention has accomplished based on the finding.

Thus, according to the present invention, there is provided a method for producing a cycloalkanol by hydrating a cycloalkene having 5–8 carbon atoms with a catalyst obtained by ion-exchanging all or a part of the ion-exchangeable cations of a crystalline gallium silicate with hydrogen ions, said gallium silicate (1) having the general formula, $xMnO\cdot Ga_2O_3\cdot ySiO_2\cdot zH_2O$ (wherein x represents a real number of from 0.7 to 1.1, M represents a cation, n represents 2/[ionic valence of the cation], y represents a real number of from 5 to 300, z represents a real number of from 0 to 200), and (2) characterized in that X-ray diffractometry thereof gives main peaks showing the following lattice spacings and relative intensities data,

TABLE 1

| Lattice spacing (Å) | Relative intensity (I/I₀) |
|---|---|
| 11.1 ± 0.3 | Strong |
| 10.0 ± 0.3 | Strong |
| 3.85 ± 0.1 | Strongest |
| 3.75 ± 0.1 | Strong |
| 3.65 ± 0.1 | Medium |

The cycloalkenes used as the starting material in the present invention are those having 5–8 carbon atoms. Specific examples thereof are cyclopentene, cyclohexene, cyclooctene and the like.

The catalysts used in the present invention are those obtained by ion-exchanging all or a part of the ion-exchangeable cations of a crystalline gallium silicate with hydrogen ions, said gallium silicate (1) having the general formula, $xMnO\cdot Ga_2O_3\cdot ySiO_2\cdot zH_2O$ (wherein x represents a real number of from 0.7 to 1.1, M represents a cation, n represents 2/[ionic valence of the cation], y represents a real number of from 5 to 300, preferably 20 to 100, z represents a real number of from 0 to 200), and (2) characterized in that X-ray diffractometry thereof gives main peaks showing the following lattice spacings and relative intensities data,

TABLE 1

| Lattice spacing (Å) | Relative intensity (I/I₀) |
|---|---|
| 11.1 ± 0.3 | Strong |
| 10.0 ± 0.3 | Strong |
| 3.85 ± 0.1 | Strongest |
| 3.75 ± 0.1 | Strong |
| 3.65 ± 0.1 | Medium |

Species of the ion-exchangeable cations are not critical if they are ion-exchangeable with hydrogen ions. Usually they are alkaline metal ions, alkaline earth metal ions, quarternary ammonium ions including organic ammonium ions and the like.

In preparing the catalyst, using tetra-n-propylammonium salt gives a catalyst used in the present invention showing a specific X-ray diffraction pattern. Catalysts prepared by using a crystalline gallium silicate showing a different X-ray diffraction pattern give a lower yield of alkanol than gives the catalyst prepared by using a crystalline gallium silicate showing the specific pattern.

The crystalline gallium silicate is prepared by a known method. For example, it can be prepared according to any of the methods disclosed in "Journal of Molecular Catalysis", Vol. 31, pp. 355–370 (1985); JP-A-56-16427; JP-A-56-26822; JP-A-57-158730; JP-A-58-110418 and the like.

Any known method can be applicable for ion-exchanging the ion-exchangeable cations of a crystalline gallium silicate with hydrogen ions. For instance, the ion-exchangeable cations can be ion-exchanged with ammonium ions which are in turn converted to hydrogen ions by thermal decomposition.

The amount of water used in the hydration reaction is usually about 1–100 moles, preferably about 5–20 moles per mole of cycloalkene.

The method of the present invention can be carried out by a batch-wise or continuous reaction. When the continuous reaction is applied, both a catalyst-packed, continuous flow method and a stirrer flow method can be employed.

The weight ratio of the catalyst to cycloalkene is, at a batch-wise reaction, usually about 0.01–200, preferably 0.1–20.

The method of the present invention can be carried out in the coexistence of aliphatic saturated hydrocarbons, aromatic hydrocarbons, alcohols, ketones, esters, organic compounds containing a halogen, organic compounds containing sulfur, phenols and the like other than the cycloalkene, catalyst and water.

Specific examples of phenols are phenol, cresol, xylenol, ethylphenol, trimethylphenol, isopropylphenol, chlorophenol, phenylphenol, nitrophenol, t-butylphenol, salicylic acid, pyrocatechol, naphthol and the like. Cresol, chlorophenol and nitrophenol are preferred.

When phenols are coexisted in the reaction, the amount is usually from about 0.01 to 10 parts by weight, preferably from 0.1 to 2 parts by weight relative to the amount of cycloalkene used.

The hydration reaction is carried out at a temperature of about 50°–200° C., preferably 70°–150° C. A temperature lower than 50° C. cannot drive the reaction rapidly so that such a temperature is not practical. On the contrary, a temperature higher than 200° C. is not preferred because such a temperature shifts the chemical equilibrium toward cycloalkene and lowers the yield of cycloalkanol.

The reaction can be carried out at normal pressures or under a pressure. Though the reaction pressure is preferred to be high enough to keep cycloalkene in liquid phase, it may be low if it can make cycloalkene dissolve in a solvent. An inert gas such as nitrogen gas and the like can control the pressure.

The following examples serve to give specific illustrations of the practice of the present invention but they are not intended in any way to limit the scope of the present invention. In the examples, the yield of cycloalkanol is calculated according to the following equation.

$$\text{Yield}(\%) = \frac{\text{Number of moles of cycloalkanol charged}}{\text{Number of moles of cycloalkene charged}} \times 100$$

REFERENTIAL EXAMPLE 1

The catalyst was prepared as follows.

The material liquid mixtures having the following compositions were prepared.

| Liquid mixture A | |
|---|---|
| Water | 190 g |
| $H_2SO_4$ | 9.3 g |
| $Ga(NO_3)_3 \cdot xH_2O$ | 4.8 g |
| $(n-Pr)_4NBr$ | 13.9 g |
| NaCl | 32.9 g |
| Liquid mixture B | |
| Water | 139 g |
| sodium silicate | |
| ($Na_2O$ content: 9.2%, | |
| $SiO_2$ content: 29.0%) | 111 g |

The above liquid mixtures A and B were mixed. The mixture was charged into a 1-liter stainless steel autoclave. Then, with stirring the mixture with a stirrer (600–700 rpm), the hydrothermal reaction was carried out at first at 120° C. for 72 hours and then at 160° C. for 5 hours. After having been cooled, the mixture was filtered, thoroughly washed with a large volume (about 3 liters) of water and filtered again. Drying the resulting cake at 120° C. for 15 hours followed by calcining the dried cake at 550° C. for 3 hours under air atmosphere gave a white powdery crystal. This crystal had a composition approximately represented by the formula, $Na_2O \cdot Ga_2O_3 \cdot 58SiO_2$.

Table 2 shows the result of X-ray diffractometry of the crystal.

Then 10 g of the above-obtained crystal were ion-exchanged with 100 g of 5% aqueous solution of ammonium chloride at 60° C. for one hour. This procedure was repeated four times. Thereafter the ion-exchanged crystal was filtered and washed with water. Drying the cake at 120° C. for 16 hours followed by calcining the dried cake at 500° C. for 3 hours under air atmosphere gave a catalyst of which more than 90% of sodium ions had been ion-exchanged with hydrogen ions.

TABLE 2

| $2\theta$ | d (Å) | $I/I_0$ | $2\theta$ | d (Å) | $I/I_0$ |
|---|---|---|---|---|---|
| 7.80 | 11.33 | 82 | 26.50 | 3.36 | 13 |
| 8.70 | 10.16 | 60 | 26.80 | 3.32 | 15 |
| 9.74 | 9.07 | 7 | 27.34 | 3.26 | 8 |
| 11.74 | 7.53 | 9 | 28.32 | 3.15 | 7 |
| 12.42 | 7.12 | 6 | 29.14 | 3.06 | 15 |
| 13.06 | 6.77 | 10 | 29.84 | 2.99 | 19 |
| 13.80 | 6.41 | 18 | 31.10 | 2.87 | 7 |
| 14.64 | 6.05 | 22 | 31.62 | 2.83 | 7 |
| 15.40 | 5.75 | 15 | 32.62 | 2.74 | 8 |
| 15.76 | 5.62 | 17 | 34.26 | 2.62 | 8 |
| 16.38 | 5.41 | 8 | 35.58 | 2.52 | 7 |
| 17.18 | 5.16 | 6 | 36.02 | 2.49 | 9 |
| 17.60 | 5.04 | 11 | 37.12 | 2.42 | 6 |
| 19.12 | 4.64 | 10 | 37.42 | 2.40 | 7 |
| 20.24 | 4.38 | 13 | 44.98 | 2.01 | 12 |
| 20.74 | 4.28 | 16 | 45.40 | 2.00 | 13 |
| 21.62 | 4.11 | 7 | 46.36 | 1.96 | 2 |
| 22.06 | 4.03 | 11 | 44.34 | 1.92 | 6 |
| 22.98 | 3.87 | 100 | 48.56 | 1.87 | 6 |
| 23.80 | 3.74 | 55 | 51.76 | 1.76 | 5 |
| 24.28 | 3.66 | 33 | 54.88 | 1.67 | 6 |
| 25.78 | 3.45 | 14 | | | |

REFERENTIAL EXAMPLE 2

An ion-exchanged aluminosilicate catalyst was prepared as follows.

The material liquid mixtures having the following compositions were prepared.

| Liquid mixture A | |
|---|---|
| Water | 271 g |
| $H_2SO_4$ | 13.2 g |
| $Al_2(SO_4)_3 \cdot 16\text{-}18H_2O$ | 4.6 g |
| $(n-Pr)_4NBr$ | 19.9 g |
| NaCl | 46.9 g |
| Liquid mixture B | |
| Water | 198 g |
| Sodium silicate | |
| ($Na_2O$ content: 9.2%, | |
| $SiO_2$ content: 29.0%) | 159 g |

The above liquid mixtures A and B were mixed. The mixture was charged into a 1-liter stainless steel autoclave. Then, with stirring the mixture with a stirrer (600–700 rpm), the hydrothermal reaction was carried out at first at 120° C. for 72 hours and then at 160° C. for 5 hours. After having been cooled, the mixture was filtered, thoroughly washed with a large volume (about 3 liters) of water and filtered again. Drying the resulting cake at 120° C. for 15 hours followed by calcining the dried cake at 550° C. for 3 hours under air atmosphere gave a white powdery crystal. The X-ray diffractometry demonstrated that the crystal was ZSM-5.

Then 10 g of the above-obtained sodium-type ZSM-5 were ion-exchanged with 100 g of 5% aqueous solution of ammonium chloride at 60° C. for one hour. This procedure was repeated four times. Thereafter the ion-exchanged ZSM-5 was filtered and washed with water. Drying the cake at 120° C. for 16 hours followed by calcining the dried cake at 500° C. for 3 hours under air atmosphere gave a catalyst ion-exchanged with hydrogen ions.

EXAMPLE 1

0.6 g of the catalyst obtained in Referential Example 1, 0.9 g of cyclohexene and 1.8 g of water were charged into a glass ampoule tube having an inner volume of 10 ml. The ampoule tube was sealed and the reaction was carried out at 120° C. for 2 hours.

After having been cooled, the ampoule tube was unsealed to take out the reaction product. Then n-propanol was added thereto to uniformly mix the aqueous phase and organic phase. Gas chromatographing the same showed a yield of cyclohexanol of 13.9%.

COMPARATIVE EXAMPLE

The same procedure as in Example 1 was repeated except that the catalyst was replaced by the catalyst obtained in Referential example 2. The yield of cyclohexanol was 12.4%.

EXAMPLE 2

0.6 g of the catalyst obtained in Referential Example 1, 0.9 g of cyclohexene, 1.8 g of water and 0.3 g of m-cresol were charged into a glass ampoule tube having an inner volume of 10 ml. The ampoule tube was sealed and the reaction was carried out at 120° C. for 2 hours.

After having been cooled, the ampoule tube was unsealed to take out the reaction product. Then n-propanol was added thereto to uniformly mix the aqueous phase and organic phase. Gas chromatographing the same showed a yield of cyclohexanol of 29.5%.

EXAMPLE 3

The same procedure as in Example 2 was repeated except that m-cresol was replaced by p-chlorophenol. The yield of cyclohexanol was 32.6%.

EXAMPLE 4

The same procedure as in Example 2 was repeated except that m-cresol was replaced by p-nitrophenol. The yield of cyclohexanol was 32.9%.

We claim:

1. A method for producing a cycloalkanol by hydrating a cycloalkene having 5–8 carbon atoms with water at a temperature in the range of 50°–200° C. in the presence of a catalyst obtained by ion-exchanging all or a part of the ion-exchangeable cations of a crystalline gallium silicate with hydrogen ions, said gallium silicate (1) having the general formula, $xMnO \cdot Ga_2O_3 \cdot ySiO_2 \cdot zH_2O$ (wherein x represents a real number of from 0.7 to 1.1, M represents a cation, n represents 2/, y represents a real number of from 5 to 300, z represents a real number of from 0 to 200), and (2) being characterized in that X-ray diffractometry thereof gives main peaks showing the following lattice spacings and relative intensities data,

| Lattice spacing (Å) | Relative intensity ($I/I_0$) |
| --- | --- |
| 11.1 ± 0.3 | Strong |
| 10.0 ± 0.3 | Strong |
| 3.85 ± 0.1 | Strongest |
| 3.75 ± 0.1 | Strong |
| 3.65 ± 0.1 | Medium |

2. A method according to claim 1, wherein M represents sodium ion, n represents 2, x represents 1, y represents 58, z represents 0 in the general formula.

3. A method according to claim 1, wherein 90% or more of the ion-exchangeable cations of the crystalline silicate are ion-exchanged with hydrogen ions.

4. A method according to claim 1, wherein the ion-exchangeable cations are alkaline metal ions, alkaline earth metal ions or quaternary ammonium ions including organic ammonium ions.

5. A method according to claim 1, wherein the ion-exchangeable cations are quaternary ammonium ions including organic ammonium ions.

6. A method according to claim 1, wherein the ion-exchangeable cations are tetra-n-propylammonium ions.

7. A method according to claim 1, wherein the cycloalkene is cyclopentene, cyclohexene or cyclooctene.

8. A method according to claim 1, wherein the cycloalkene is cyclohexene.

9. A method for producing a cycloalkanol by hydrating a cycloalkene having 5–8 carbon atoms with water at a temperature in the range of 50°–200° C. in the presence of at least one phenol and a catalyst obtained by ion-exchanging all or a part of the ion-exchangeable cations of a crystalline gallium silicate with hydrogen ions, said gallium silicate
   (1) having the general formula, $xMnO \cdot Ga_2O_3 \cdot ySiO_2 \cdot zH_2O$ (wherein x represents a real number of from 0.7 to 1.1, M represents a cation, n represents 2/, y represents a real number of from 5 to 300, z represents a real number of from 0 to 200), and
   (2) being characterized in that X-ray diffractometry thereof gives main peaks showing the following lattice spacings and relative intensities data,

| Lattice spacing (Å) | Relative intensity ($I/I_0$) |
| --- | --- |
| 11.1 ± 0.3 | Strong |
| 10.0 ± 0.3 | Strong |
| 3.85 ± 0.1 | Strongest |
| 3.75 ± 0.1 | Strong |
| 3.65 ± 0.1 | Medium |

10. A method according to claim 9, wherein the phenol is at least one phenol selected from the group consisting of phenol, cresol, xylenol, ethylphenol, trimethylphenol, isopropylphenol, chlorophenol, phenylphenol, nitrophenol, t-butylphenol, salicylic acid, pyrocatechol and naphthol.

11. A method according to claim 9, wherein the phenol is cresol, chlorophenol or nitrophenol.

* * * * *